United States Patent
Takahashi et al.

(10) Patent No.: US 11,682,761 B2
(45) Date of Patent: Jun. 20, 2023

(54) NICKEL HYDROXIDE, POSITIVE ELECTRODE MATERIAL, ALKALINE BATTERY, AND METHOD OF PRODUCING NICKEL HYDROXIDE

(71) Applicants: TOYOTA JIDOSHA KABUSHIKI KAISHA, Toyota (JP); NATIONAL RESEARCH COUNCIL OF CANADA, Ottawa (CA)

(72) Inventors: Kenji Takahashi, Toyota (JP); Christina Bock, Quebec (CA); Nafiseh Ebrahimi, Ontario (CA); Olga Naboka, Ontario (CA)

(73) Assignees: TOYOTA JIDOSHA KABUSHIKI KAISHA, Toyota (JP); NATIONAL RESEARCH COUNCIL OF CANADA, Ottawa (CA)

( * ) Notice: Subject to any disclaimer, the term of this patent is extended or adjusted under 35 U.S.C. 154(b) by 240 days.

(21) Appl. No.: 16/913,655

(22) Filed: Jun. 26, 2020

(65) Prior Publication Data

US 2020/0411855 A1     Dec. 31, 2020

(30) Foreign Application Priority Data

Jun. 28, 2019    (JP) .............................. JP2019-121517

(51) Int. Cl.
*H01B 1/06*        (2006.01)
*H01M 4/52*       (2010.01)
(Continued)

(52) U.S. Cl.
CPC .............. *H01M 4/52* (2013.01); *C01B 25/45* (2013.01); *C01B 35/128* (2013.01); *C01G 53/04* (2013.01);
(Continued)

(58) Field of Classification Search
CPC ... H01B 1/00; H01B 1/06; H01B 1/08; C01G 53/04; H01M 4/52
See application file for complete search history.

(56) References Cited

U.S. PATENT DOCUMENTS

| | | | |
|---|---|---|---|
| 5,905,003 A | * | 5/1999 | Young ..................... C01G 53/04 429/223 |
| 6,019,955 A | | 2/2000 | Ovshinsky et al. |

(Continued)

FOREIGN PATENT DOCUMENTS

| | | |
|---|---|---|
| CN | 103682475 A | 3/2014 |
| CN | 107851785 A | 3/2018 |

(Continued)

OTHER PUBLICATIONS

Mavis et al "Cyanate intercalation in nickel hydroxide", Chem. Mater. 2006, 18, 5317-5325.*

(Continued)

*Primary Examiner* — Mark Kopec
(74) *Attorney, Agent, or Firm* — Sughrue Mion, PLLC (57) ABSTRACT

A nickel hydroxide includes stacked nickel hydroxide layers. Each of the nickel hydroxide layers includes $Ni^{2+}$ and $OH^-$. At least one of the nickel hydroxide layers further includes a type of polyatomic anions. The polyatomic anions include a type of anions that are not $SO_4^{2-}$ or $CO_3^{2-}$.

12 Claims, 4 Drawing Sheets

(51) Int. Cl.

| | | |
|---|---|---|
| *C01G 53/04* | (2006.01) | |
| *C01B 25/45* | (2006.01) | |
| *C01B 35/12* | (2006.01) | |
| *C07C 55/22* | (2006.01) | |
| *H01M 4/58* | (2010.01) | |
| *H01M 4/60* | (2006.01) | |
| *H01M 10/30* | (2006.01) | |
| *H01M 4/02* | (2006.01) | |

(52) U.S. Cl.
CPC .............. *C07C 55/22* (2013.01); *H01B 1/06* (2013.01); *H01M 4/5825* (2013.01); *H01M 4/60* (2013.01); *H01M 10/30* (2013.01); *C01P 2002/22* (2013.01); *C01P 2002/88* (2013.01); *C01P 2006/40* (2013.01); *H01M 2004/028* (2013.01)

(56) References Cited

U.S. PATENT DOCUMENTS

2016/0233506 A1* 8/2016 Young .................... H01M 4/32
2018/0226636 A1   8/2018 Sawa et al.

FOREIGN PATENT DOCUMENTS

| EP | 0 388 808 A2 | 9/1990 |
|---|---|---|
| JP | 2010-153261 A | 7/2010 |

OTHER PUBLICATIONS

Lee et al "Hierarchial microspheres based on alpha-Ni(OH)2 nanosheets intercalated with different anions . . . ", Journal of Physical Chemistry C 2011, 115, 19445-19454.*
Hall et al "Nickel hydroxides and related materials; a review of their structure, synthesis and properties", Proc. R. Soc. A 471: 20140792 (2014).*
Alcantara et al "Lithium-nickel citrate precursors . . . ", Chem. Mater. Sep. 1997, 2145-55.*
Kameda et al, "Ni Al layered double hydroxides modified with citrate, malate, and tartrate: Preparation by coprecipitation and uptake of $Cu^{2+}$ from aqueous solution", Journal of Physics and Chemistry of Solids, vol. 72, Mar. 2011, pp. 846-851.
Das et al, "Adsorption of phosphate by layered double hydroxides in aqueous solutions", Applied Clay Science, vol. 32, May 2006, pp. 252-260.
Rojas et al., "Layered Ni(II)—Zn(II) Hydroxyacetates. Anion Exchange and Thermal Decomposition of The Hydroxysalts Obtained", Journal of Materials Chemistry, vol. 12, Jan. 2002, pp. 1071-1078.
Wang et al., "Synthesis and characterization of a layered double hydroxide containing an intercalated nickel(II) citrate complex", Materials Chemistry and Physics, vol. 104, Jun. 2007, pp. 133-140.
Maki et al., "Anion-exchange properties of nickel-aluminum layered double hydroxide prepared by liquid phase deposition", Materials Chemistry and Physics, vol. 141, Jun. 2013, pp. 445-453.
Su et al., "Borate-ion intercalated Ni—Fe layered double hydroxide to simultaneously boost mass transport and charge transfer for catalysis of water oxidation", Journal of Colloid and Interface Science, 2018, vol. 528, pp. 36-44 (9 pages total).
Mostafa Taibi et al., "Layered nickel hydroxide salts: synthesis, characterization and magnetic behaviour in relation to the basal spacing", Journal of Materials Chemistry, 2002, vol. 12, pp. 3238-3244 (7 pages total).

* cited by examiner

NICKEL HYDROXIDE, POSITIVE ELECTRODE MATERIAL, ALKALINE BATTERY, AND METHOD OF PRODUCING NICKEL HYDROXIDE

This nonprovisional application is based on Japanese Patent Application No. 2019-121517 filed on Jun. 28, 2019, with the Japan Patent Office, the entire contents of which are hereby incorporated by reference.

BACKGROUND

Field

The present disclosure relates to a nickel hydroxide, a positive electrode material, an alkaline battery, and a method of producing a nickel hydroxide.

Description of the Background Art

Japanese Patent Laying-Open No. 2010-153261 discloses a nickel-metal hydride battery.

SUMMARY

Operating voltage of a battery is the difference between the operating potential of positive electrode material and the operating potential of negative electrode material. According to the applications of the battery, for example, there is a demand for adjusting the operating voltage of the battery. Conventionally, as a positive electrode material of alkaline batteries, nickel hydroxide [$Ni(OH)_2$] is used.

An object of the present disclosure is to control the operating potential of nickel hydroxide.

In the following, the technical structure and the effects according to the present disclosure are described. It should be noted that the action mechanism according to the present disclosure includes presumption. Therefore, the scope of claims should not be limited by whether or not the action mechanism is correct.

[1] A nickel hydroxide according to the present disclosure includes stacked nickel hydroxide layers. Each of the nickel hydroxide layers includes nickel ions and hydroxide ions. At least one of the nickel hydroxide layers further includes a type of polyatomic anions. The polyatomic anions include a type of anions that are not sulfate ions or carbonate ions.

Typically, nickel hydroxide [$Ni(OH)_2$] is synthesized via reactive crystallization. In reactive crystallization, an aqueous solution of nickel sulfate ($NiSO_4$) and an aqueous solution of an ammonium salt are mixed to prepare an aqueous solution containing a nickel ammine complex, and to the resulting aqueous solution, an aqueous solution of sodium hydroxide (NaOH) is added to precipitate nickel hydroxide. In the synthesis, sodium carbonate ($Na_2CO_3$) and the like may be used as a pH regulator.

The nickel hydroxide is a layered compound. The nickel hydroxide includes stacked nickel hydroxide layers that include nickel ions ($Ni^{2+}$) and hydroxide ions ($OH^-$). The nickel hydroxide layers may be positively charged. Between the nickel hydroxide layers, anions responsible for charge compensation (hereinafter, also called "intercalated anions") may be present. Between the layers, water ($H_2O$) and the like having no charge may also be present.

The intercalated anions responsible for charge compensation may be polyatomic anions derived from a raw material and the like. The "polyatomic anion" according to the present disclosure refers to an anion consisting of two or more atoms (except $OH^-$). The polyatomic anions derived from a raw material and the like may be sulfate ions ($SO_4^{2-}$) and carbonate ions ($CO_3^{2-}$). Part of the $SO_4^{2-}$ and $CO_3^{2-}$ may not serve as intercalated anions but instead replace $OH^-$ in the nickel hydroxide layers. In other words, $SO_4^{2-}$ and $CO_3^{2-}$ may be incorporated in the structure of the nickel hydroxide layers.

In the nickel hydroxide according to the present disclosure, $OH^-$ in the nickel hydroxide layers is partially replaced by the polyatomic anions that are not $SO_4^{2-}$ or $CO_3^{2-}$. Hereinafter, the "polyatomic anions that are not $SO_4^{2-}$ or $CO_3^{2-}$" are also called "particular polyatomic anions".

With the particular polyatomic anions incorporated in the structure of the nickel hydroxide layers, the nickel hydroxide according to the present disclosure may have an operating potential that is different from the operating potential of an ordinary nickel hydroxide. According to a novel finding of the present disclosure, the operating potential changes depending on the type of the particular polyatomic anions. Therefore, changing the type of the particular polyatomic anions may achieve control over the operating potential.

[2] The polyatomic anions may include a type of organic anions. [3] The organic anions may include at least one type selected from the group consisting of citrate ions and acetate ions.

With such particular polyatomic anions incorporated in the structure of the nickel hydroxide layers, the operating potential may be increased.

[4] The organic anions may be citrate ions.

With citrate ions incorporated in the structure of the nickel hydroxide layers, the memory effect may be less likely to occur in the alkaline battery. With the memory effect being less likely to occur, control over the operating potential may be improved.

[5] The polyatomic anions may include a type of inorganic anions.

[6] The inorganic anions may include at least one type selected from the group consisting of phosphate ions and tetraborate ions.

With such particular polyatomic anions incorporated in the structure of the nickel hydroxide layers, the operating potential may be decreased.

[7] At least one of the nickel hydroxide layers may further include aluminum ions.

With aluminum ions ($Al^{3+}$) incorporated in the structure of the nickel hydroxide layers, the operating potential may change. Combining the particular polyatomic anions with $Al^{3+}$ may achieve control over the operating potential.

[8] A positive electrode material according to the present disclosure includes at least the nickel hydroxide according to any one of [1] to [7] above.

[9] An alkaline battery according to the present disclosure includes at least the positive electrode material according to [8] above.

[10] A method of producing a nickel hydroxide according to the present disclosure includes the following (A) and (B):

(A) preparing a raw material liquid containing at least nickel ions, hydroxide ions, and a type of polyatomic anions; and (B) synthesizing a nickel hydroxide by adjusting a pH of the raw material liquid.

The polyatomic anions include at least one type selected from the group consisting of:

a type of anions that are not sulfate ions or carbonate ions;
sulfate ions; and
carbonate ions.

The method of producing a nickel hydroxide according to the present disclosure further includes (C) performing hydrothermal treatment on the nickel hydroxide when the polyatomic anions do not include the anions that are not sulfate ions or carbonate ions.

In the method of producing a nickel hydroxide according to the present disclosure, the particular polyatomic anions may be incorporated in the structure of the nickel hydroxide layers. Changing the type of the particular polyatomic anions may achieve control over the operating potential.

In the method of producing a nickel hydroxide according to the present disclosure, even when the particular polyatomic anions are not incorporated in the structure of the nickel hydroxide layers, the operating potential may still be controlled. It is because when the polyatomic anions do not include the particular polyatomic anions, hydrothermal treatment is performed on the nickel hydroxide; the hydrothermal treatment may change crystallinity of the nickel hydroxide; and consequently an increase in the operating potential may occur, for example.

[11] The method of producing a nickel hydroxide according to the present disclosure may further include performing hydrothermal treatment on the nickel hydroxide when the polyatomic anions include the anions that are not sulfate ions or carbonate ions.

Combining incorporation of the particular polyatomic anions with the hydrothermal treatment may achieve control over the operating potential.

[12] The raw material liquid may be prepared by mixing an aqueous solution of nickel sulfate, an aqueous solution of a salt of sodium ions and the polyatomic anions, and an aqueous solution of sodium hydroxide.

[13] The raw material liquid may be prepared by mixing an aqueous solution of a salt of nickel ions and the polyatomic anions and an aqueous solution of sodium hydroxide.

[14] The polyatomic anions may include a type of organic anions.

[15] The organic anions may include at least one type selected from the group consisting of citrate ions and acetate ions.

[16] The organic anions may be citrate ions.

[17] The polyatomic anions may include a type of inorganic anions.

[18] The inorganic anions may include at least one type selected from the group consisting of phosphate ions and tetraborate ions.

[19] The raw material liquid may further contain aluminum ions.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

In the following, embodiments according to the present disclosure (herein called "present embodiment") are described. However, the description below does not limit the scope of claims.

<Nickel Hydroxide>

A nickel hydroxide according to the present embodiment may be typically used as a positive electrode material of an alkaline battery. However, applications of the nickel hydroxide according to the present embodiment are not limited to positive electrode material. The nickel hydroxide according to the present embodiment may also be used in applications other than positive electrode material.

Typically, the nickel hydroxide according to the present embodiment is a group of particles (powder). The particle size of the nickel hydroxide is not particularly limited. The d50 of the nickel hydroxide may range from 1 μm to 30 μm, for example. The "d50" according to the present embodiment refers to a particle size in volume-based particle size distribution at which the cumulative particle volume (accumulated from the side of small sizes) reaches 50% of the total particle volume. The volume-based particle size distribution may be measured by laser diffraction and scattering, for example.

<<Structure>>

Figure 1:
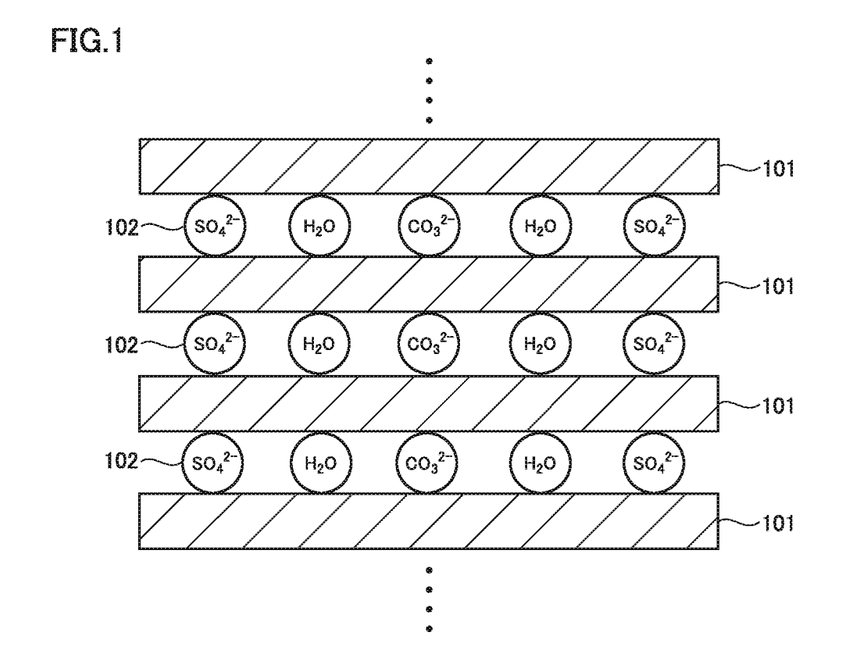
FIG. 1 is a conceptual view of a structure of the nickel hydroxide according to the present embodiment.

FIG. 1 is a conceptual view of a structure of the nickel hydroxide according to the present embodiment.

The nickel hydroxide may be a crystalline substance. The nickel hydroxide may have $\beta$-Ni(OH)$_2$ structure, for example. The nickel hydroxide may have $\alpha$-Ni(OH)$_2$ structure, for example. In the nickel hydroxide, a phase having $\beta$-Ni(OH)$_2$ structure and a phase having $\alpha$-Ni(OH)$_2$ structure may coexist, for example. The nickel hydroxide may be amorphous.

The nickel hydroxide is a layered compound. The nickel hydroxide includes stacked nickel hydroxide layers 101. Each of nickel hydroxide layers 101 includes Ni$^{2+}$ and OH$^-$. Each of nickel hydroxide layers 101 may be positively charged.

Between nickel hydroxide layers 101, intercalated anions 102 are present. Intercalated anions 102 may be SO$_4^{2-}$ and/or CO$_3^{2-}$, for example. Intercalated anions 102 may be responsible for charge compensation of the positive charge of nickel hydroxide layers 101. In addition to intercalated anions 102, H$_2$O and the like may further be present between nickel hydroxide layers 101.

In the nickel hydroxide according to the present embodiment, OH$^-$ in nickel hydroxide layers 101 is partially replaced by particular polyatomic anions. More specifically, at least one of nickel hydroxide layers 101 further includes particular polyatomic anions. The particular polyatomic anions according to the present embodiment are anions that are not SO$_4^{2-}$ or CO$_3^{2-}$.

In the nickel hydroxide according to the present embodiment, substantially all the nickel hydroxide layers 101 may include the particular polyatomic anions. In the nickel hydroxide according to the present embodiment, nickel hydroxide layers 101 including the particular polyatomic anions and nickel hydroxide layers 101 not including the particular polyatomic anions may coexist.

In the nickel hydroxide according to the present embodiment, as long as at least one of nickel hydroxide layers 101 includes the particular polyatomic anions, nickel hydroxide layers 101 may further include $SO_4^{2-}$ and $CO_3^{2-}$.

<<Particular Polyatomic Anions>>

The particular polyatomic anions according to the present embodiment may be incorporated in the structure of the nickel hydroxide layers. The particular polyatomic anions incorporated in the structure are differentiated from the intercalated anions responsible for charge compensation.

The nickel hydroxide layers may be represented by, for example, the following formula (I):

$$Ni(OH)_x(Anion)_y \quad (I)$$

[where Anion denotes the particular polyatomic anions; x and y satisfy the relation "x+ny=2"; and n denotes the valence of the particular polyatomic anions].

In the above formula (I), y denotes the amount of replacement by the particular polyatomic anions. y may satisfy "0<y≤0.20", for example. y may satisfy "0.05≤y≤0.20", for example. y may satisfy "0.05≤y≤0.10", for example. n may be 1, 2, or 3.

x and y in the above formula (I) may be determined by TGA-FTIR, for example. The "TGA-FTIR" refers to an analysis technique that involves performing thermal gravimetric analysis (TGA) while identifying off-gas with a fourier transform infrared spectrometer (FTIR).

According to a novel finding of the present disclosure, the operating potential may change depending on the type of the particular polyatomic anions. Only one type of the particular polyatomic anions may be incorporated in the nickel hydroxide layers. Two or more types of the particular polyatomic anions may be incorporated in the nickel hydroxide layers.

The particular polyatomic anions may include organic anions, for example. The "organic anion" according to the present embodiment refers to a polyatomic anion containing a carbon atom (C). The organic anions may include at least one type selected from the group consisting of citrate ions [C(OH)(CH$_2$COO$^-$)$_2$COO$^-$] and acetate ions (CH$_3$COO$^-$), for example. Such organic anions may be incorporated in the structure of the nickel hydroxide layers. With such organic anions incorporated in the structure of the nickel hydroxide layers, the operating potential may be increased.

Some organic anions are difficult to incorporate in the structure of the nickel hydroxide layers. For example, oxalate ions [(COO$^-$)$_2$] are difficult to incorporate in the nickel hydroxide layers.

The organic anions may be citrate ions. With citrate ions incorporated in the structure of the nickel hydroxide layers, the memory effect may be less likely to occur in the alkaline battery.

The citrate ions may be monovalent anions [C(OH)(CH$_2$COOH)$_2$COO$^-$]. The citrate ions may be divalent anions [C(OH)(CH$_2$COO)$_2$COO$^-$]. The citrate ions may be trivalent anions [C(OH)(CH$_2$COO)$_2$COO$^-$].

The particular polyatomic anions may include inorganic anions, for example. The "inorganic anion" according to the present embodiment refers to a polyatomic anion containing no carbon atom. The inorganic anions may include at least one type selected from the group consisting of phosphate ions ($PO_4^{3-}$) and tetraborate ions ($B_4O_7^{2-}$), for example. Such inorganic anions may be incorporated in the structure of the nickel hydroxide layers. With such inorganic anions incorporated in the structure of the nickel hydroxide layers, the operating potential may be decreased.

Some inorganic anions are difficult to incorporate in the structure of the nickel hydroxide layers. For example, nitrate ions ($NO_3^-$) are difficult to incorporate in the nickel hydroxide layers.

<<Cation Replacement>>

In the nickel hydroxide according to the present embodiment, $Ni^{2+}$ in the nickel hydroxide layers may be partially replaced by $Al^{3+}$. More specifically, at least one of the nickel hydroxide layers may further include $Al^{3+}$. With $Ni^{2+}$ partially replaced by $Al^{3+}$, the operating potential may change.

In the nickel hydroxide according to the present embodiment, substantially all the nickel hydroxide layers 101 may include $Al^{3+}$. In the nickel hydroxide according to the present embodiment, nickel hydroxide layers 101 including $Al^{3+}$ and nickel hydroxide layers 101 not including $Al^{3+}$ may coexist.

When $Al^{3+}$ is incorporated in the nickel hydroxide layers, the nickel hydroxide layers may be represented by, for example, the following formula (II):

$$Ni_{1-z}Al_z(OH)_x(Anion)_y \quad (II)$$

[where Anion denotes the particular polyatomic anions; x, y, and z satisfy the relation "2+z=x+ny"; and n denotes the valence of the particular polyatomic anions]. In the above formula (II), y may satisfy "0<y≤0.20", for example, as in the above formula (I). z may satisfy "0<z≤0.25", for example. z may satisfy "0.05≤z≤0.25", for example. z may satisfy "0.05≤z≤0.15", for example. z may satisfy "0.05≤z≤0.10", for example.

x and y in the above formula (II) may be determined by TGA-FTIR, for example. z in the above formula (II) may be determined by inductively coupled plasma atomic emission spectroscopy (ICP-AES), for example.

Instead of $Al^{3+}$, cobalt ions ($Co^{3+}$, $Co^{2+}$), zinc ions (Zn+, $Zn^{2+}$), and/or the like may be used for replacing $Ni^{2+}$.

<Method of Producing Nickel Hydroxide>

Figure 2:
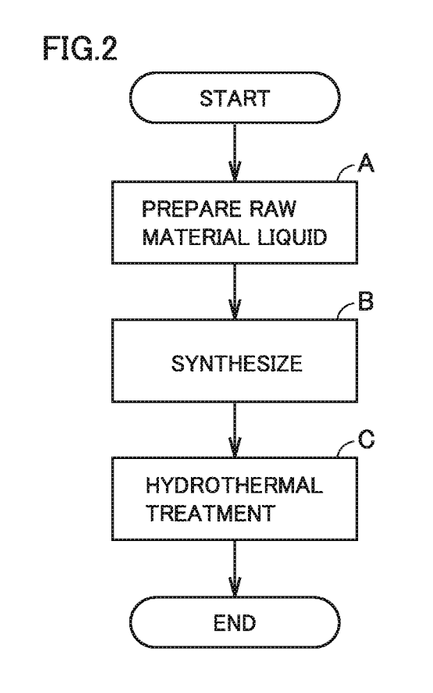
FIG. 2 is a flowchart schematically illustrating the method of producing a nickel hydroxide according to the present embodiment.

FIG. 2 is a flowchart schematically illustrating a method of producing a nickel hydroxide according to the present embodiment.

A method of producing a nickel hydroxide according to the present embodiment includes "(A) preparing a raw material liquid" and "(B) synthesizing". The method of producing a nickel hydroxide according to the present embodiment may include performing "(C) hydrothermal treatment" depending on the type of the polyatomic anions.

<<(A) Preparing Raw Material Liquid>>

The method of producing a nickel hydroxide according to the present embodiment includes preparing a raw material liquid containing at least $Ni^{2+}$, $OH^-$, and polyatomic anions. The polyatomic anions include at least one type selected from the group consisting of the particular polyatomic anions, $SO_4^{2-}$, and $CO_3^{2-}$.

The raw material liquid may be prepared by mixing various aqueous solutions, for example. In the present embodiment, a raw material liquid containing sulfate ions ($SO_4^{2-}$) may be used. In the present embodiment, the "raw material liquid containing $SO_4^{2-}$" is also called "first raw material liquid". The first raw material liquid may be prepared by mixing an aqueous solution of nickel sulfate (NiSO$_4$), an aqueous solution of a salt of sodium ions (Na+) and the particular polyatomic anions, and an aqueous solution of sodium hydroxide (NaOH), for example.

In the present embodiment, a raw material liquid not containing $SO_4^{2-}$ may also be used. In the present embodiment, the "raw material liquid not containing $SO_4^{2-}$" is also called "second raw material liquid". The second raw material liquid may be prepared by mixing an aqueous solution of a salt of $Ni^{2+}$ and the particular polyatomic anions and an aqueous solution of NaOH, for example.

The first raw material liquid and the second raw material liquid may further contain $Al^{3+}$. For example, an aqueous solution of aluminum sulfate $[Al_2(SO_4)_3]$ may be mixed in the first raw material liquid.

<<(B) Synthesizing>>

The method of producing a nickel hydroxide according to the present embodiment includes synthesizing a nickel hydroxide by adjusting a pH of the raw material liquid.

The pH of the raw material liquid may be adjusted by changing the concentrations and the amounts of various aqueous solutions added. A pH regulator may be used, for example. To the raw material liquid, ammonium hydroxide ($NH_4OH$), ammonium sulfate $[(NH_4)_2SO_4]$, sodium carbonate ($Na_2CO_3$), and/or the like may further be added, for example. The final pH of the raw material liquid may be adjusted to about 11 to about 13, for example. By this, nickel hydroxide crystals may be formed.

In the resulting nickel hydroxide, the polyatomic anions may be incorporated in the nickel hydroxide layers. When the polyatomic anions include the particular polyatomic anions, the nickel hydroxide may have an operating potential that is different from the operating potential of an ordinary nickel hydroxide.

When the polyatomic anions include the particular polyatomic anions, the nickel hydroxide may be collected at this point by filtering. After collected, the nickel hydroxide may be rinsed with water. The nickel hydroxide may be dried. The drying may be carried out in air, for example.

<<(C) Hydrothermal Treatment>>

The method of producing a nickel hydroxide according to the present embodiment includes performing hydrothermal treatment on the nickel hydroxide when the polyatomic anions do not include the particular polyatomic anions.

The method of producing a nickel hydroxide according to the present embodiment may further include performing hydrothermal treatment on the nickel hydroxide when the polyatomic anions include the particular polyatomic anions.

The hydrothermal treatment may change the crystallinity of the nickel hydroxide. For example, an increase in the crystallinity may increase the operating potential. For example, a decrease in the crystallinity may decrease the operating potential.

The hydrothermal treatment is performed in, for example, an autoclave. For example, after the nickel hydroxide is produced, the resulting nickel hydroxide may be transferred into an autoclave together with the remaining raw material liquid. The treatment temperature may be about 100° C., for example. The treatment time may be about 24 hours, for example.

After the hydrothermal treatment, the resulting nickel hydroxide is collected by filtering. After collected, the nickel hydroxide may be rinsed with water. The nickel hydroxide may be dried. The drying may be carried out in air, for example.

<Positive Electrode Material>

A positive electrode material according to the present embodiment is a positive electrode material for an alkaline battery. The positive electrode material according to the present embodiment includes at least the above-described nickel hydroxide according to the present embodiment.

The positive electrode material may consist essentially of the nickel hydroxide. However, as long as the positive electrode material includes the nickel hydroxide, the positive electrode material may further include other substances. For example, the positive electrode material may further include a cobalt compound and/or the like. For example, surfaces of particles consisting of the nickel hydroxide may be coated with a cobalt compound. The cobalt compound may be cobalt oxide, for example. The cobalt compound may improve electronic conductivity of the positive electrode material, for example.

<Alkaline Battery>

An "alkaline battery" according to the present embodiment refers to a battery including an aqueous alkali solution as electrolyte solution. The alkaline battery may be a primary battery. The alkaline battery may be a secondary battery (rechargeable battery).

As an example of the alkaline battery, a nickel-metal hydride battery is described in the present specification. However, the alkaline battery according to the present embodiment is not limited to a nickel-metal hydride battery. The alkaline battery may be a nickel-zinc battery, a nickel-cadmium battery, or a nickel-iron battery, for example.

Figure 3:
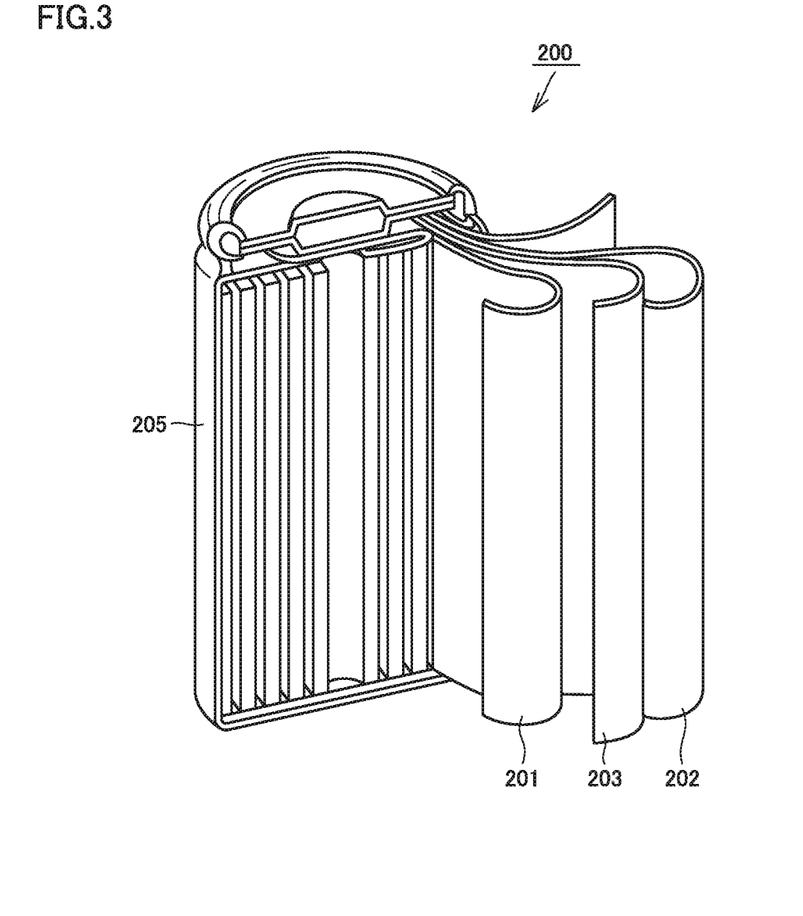
FIG. 3 is a schematic view illustrating an example configuration of the alkaline battery according to the present embodiment.

FIG. 3 is a schematic view illustrating an example configuration of the alkaline battery according to the present embodiment.

A battery 200 is a nickel-metal hydride battery. Battery 200 includes at least the positive electrode material according to the present embodiment. Therefore, battery 200 may have an operating voltage that is different from the operating voltage of an ordinary nickel-metal hydride battery. Further, depending on the type of the particular polyatomic ions, the memory effect may be less likely to occur, for example. As long as battery 200 includes the positive electrode material according to the present embodiment, other structural details are not particularly limited. The structural details described below should be regarded as mere examples.

<<Housing>>

Battery 200 includes a housing 205. Housing 205 may be made of a metal material and/or a polymer material, for example. Housing 205 is cylindrical. Alternatively, housing 205 may be prismatic. Housing 205 accommodates a positive electrode 201, a separator 203, a negative electrode 202, and an aqueous alkali solution.

<<Positive Electrode>>

Positive electrode 201 is in sheet form. In positive electrode 201, the positive electrode material according to the present embodiment is included. In addition to the positive electrode material, positive electrode 201 may further include a positive electrode current collector and a binder, for example. The positive electrode current collector may be a porous metal sheet (for example, a porous Ni sheet). For example, positive electrode 201 may be formed by filling pores of porous Ni sheets with the positive electrode material, the binder, and the like. The binder may be styrene-butadiene rubber, carboxymethylcellulose, and/or polytetrafluoroethylene, for example.

<<Negative Electrode>>

Negative electrode 202 is in sheet form. Negative electrode 202 includes at least a negative electrode material. Negative electrode 202 may further include a negative electrode current collector, a binder, and the like. The negative electrode current collector may be a perforated steel plate, for example. The perforated steel plate may have Ni plating and/or the like.

For example, negative electrode 202 may be formed by applying the negative electrode material, the binder, and the like to a surface of the negative electrode current collector. The binder may be, for example, a material described above as an example of the binder of positive electrode 201.

The negative electrode material is a hydrogen storage alloy. A hydrogen storage alloy reversibly stores and releases protium (atomic hydrogen). The hydrogen storage alloy is not particularly limited. The hydrogen storage alloy may be an $AB_5$ alloy, for example. The $AB_5$ alloy may be $LaNi_5$ and/or $MmNi_5$ ("Mm" represents misch metal), for example. Only one type of the hydrogen storage alloy may be used. Two or more types of the hydrogen storage alloy may be used in combination.

<<Separator>>

Separator 203 is interposed between positive electrode 201 and negative electrode 202. Separator 203 is electrically insulating. Separator 203 is a porous sheet. Separator 203 may be a polyolefin nonwoven fabric and/or a polyamide nonwoven fabric, for example.

<<Aqueous Alkali Solution>>

The aqueous alkali solution is an electrolyte solution. Positive electrode 201, negative electrode 202, and separator 203 are impregnated with the aqueous alkali solution. The aqueous alkali solution may be an aqueous solution of potassium hydroxide, an aqueous solution of NaOH, and/or an aqueous solution of lithium hydroxide, for example.

EXAMPLES

Next, examples according to the present disclosure are described. However, the description below does not limit the scope of claims.

Experiment 1

In Experiment 1, incorporation of polyatomic anions in the nickel hydroxide layers as well as hydrothermal treatment on the nickel hydroxide were studied. In Experiment 1, the first raw material liquid (raw material liquid containing $SO_4^{2-}$) was studied.

<<(A) Preparing Raw Material Liquid and (B) Synthesizing>>

(Sample No. 1)

Sample No. 1 is a control (control sample). A reaction vessel was prepared. In the reaction vessel, 2 M aqueous solution of NaOH (25 mL) was added. "M" denotes "mol/ L". While the aqueous solution of NaOH was being swiftly stirred with a magnetic stirrer at room temperature, 1 M aqueous solution of $NiSO_4$ (20 mL) and 0.2 M aqueous solution of $NaSO_4$ (20 mL) were added into the reaction vessel. The rate of addition was 1.7 mL/min. Thus, the first raw material liquid was prepared. The final pH of the first raw material liquid was adjusted to the range of 11 to 11.5. By this pH adjustment, the nickel hydroxide of Sample No. 1 was synthesized.

Part of the nickel hydroxide was collected, whereas the rest of the nickel hydroxide was subjected to hydrothermal treatment described below. After collected, the part of the nickel hydroxide was rinsed with water and dried in air.

(Samples Nos. 2 to 6)

As specified in Table 1 below, instead of the aqueous solution of $NaSO_4$, each of an aqueous solution of $Na_2CO_3$, an aqueous solution of $Na_3PO_4$, an aqueous solution of $Na_2B_4O_7$, an aqueous solution of sodium oxalate, and an aqueous solution of sodium citrate was used to synthesize the nickel hydroxide of Samples Nos. 2 to 6. The amount of each aqueous solution added was as specified in Table 1 below. Because 2 M aqueous solution of $Na_2B_4O_7$ was difficult to prepare, the concentration of the aqueous solution of $Na_2B_4O_7$ was set to 0.02 M.

<<(C) Hydrothermal Treatment>>

The nickel hydroxide was transferred into an autoclave together with the remaining first raw material liquid. In the autoclave, hydrothermal treatment was performed on the nickel hydroxide. The treatment temperature was 100° C. The treatment time was 24 hours. After the hydrothermal treatment, the resulting nickel hydroxide was collected. After collected, the nickel hydroxide was rinsed with water and dried in air.

<<XRD>>

For Samples Nos. 1 to 6, x-ray diffraction (XRD) patterns of the nickel hydroxide were checked. The XRD patterns were checked before and after the hydrothermal treatment. All of the XRD patterns of Samples Nos. 1 to 6 show β-Ni(OH)$_2$ structure. The full width at half maximum (FWHM) of [011] peak was used to evaluate crystallinity. Results are shown in Table 1 below. The smaller the FWHM is, the higher the crystallinity may be. In Table 1, "n/a" indicates that the peak was broad and FWHM could not be calculated.

<<TGA-FTIR>>

Figure 4:
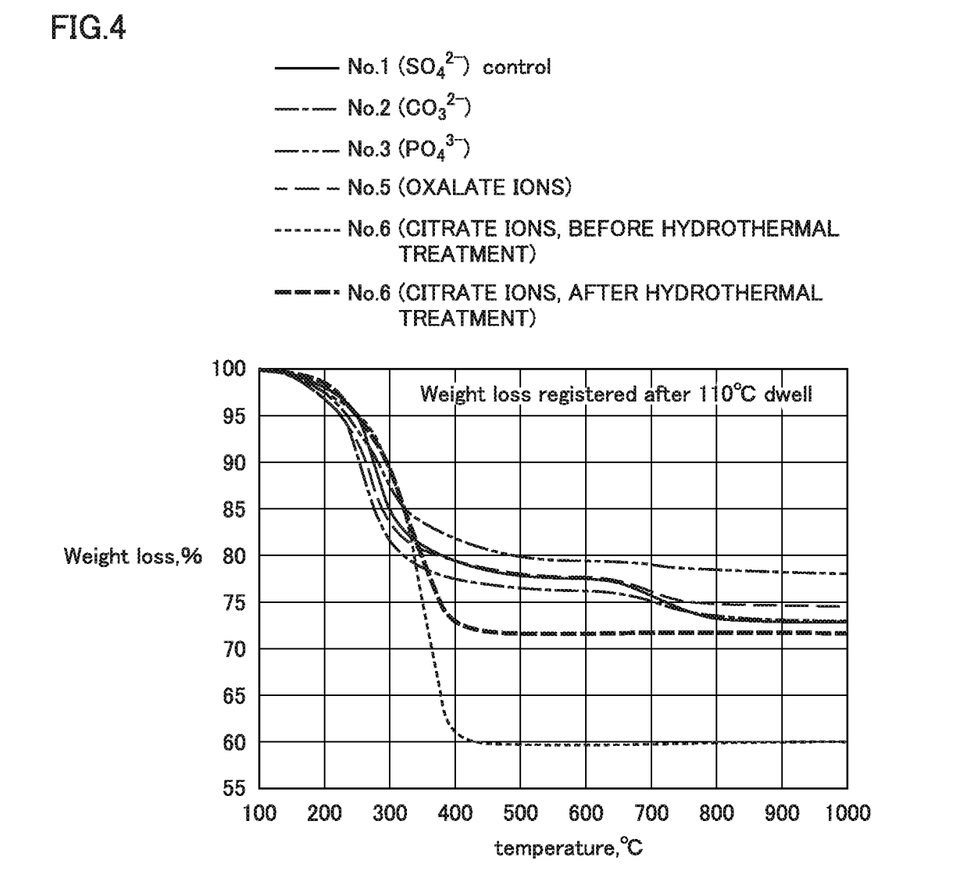
FIG. 4 illustrates TGA profiles of Samples Nos. 1 to 3, 5, and 6.

FIG. 4 illustrates TGA profiles of Samples Nos. 1 to 3, 5, and 6.

In this experiment, TGA measurement was performed after heating the sample at 110° C. for 80 minutes. The heating the sample at 110° C. for 80 minutes may remove water, carbonate, and the like adsorbed to the surface of the sample.

Sample No. 1 ($SO_4^{2-}$) showed a weight loss in three steps. The first-step weight loss occurred at 120 to 220° C. The second-step weight loss occurred at 220 to 400° C. The third-step weight loss occurred at 600 to 750° C. The FTIR data suggests that the first-step and the second-step weight losses were accompanied by release of $H_2O$ and $CO_2$. The FTIR data suggests that the third-step weight loss was accompanied by release of $SO_2$. It is considered that $SO_2$ was generated by $SO_4^{2-}$ splitting. These results suggest that $SO_4^{2-}$ was incorporated in the structure of the nickel hydroxide layers; more specifically, in Sample No. 1, at least one of the nickel hydroxide layers further included $SO_4^{2-}$ in addition to $Ni^{2+}$ and $OH^-$.

In Table 1 below, "positive" under "TGA-FTIR incorporation" indicates that the polyatomic anions may have been incorporated in the structure of the nickel hydroxide layers.

The TGA profile of Sample No. 2 ($CO_3^{2-}$) is similar to the TGA profile of Sample No. 1 ($SO_4^{2-}$). It may be because the $CO_3^{2-}$ content of the nickel hydroxide layers of Sample No. 2 was approximately the same as the $SO_4^{2-}$ content of the nickel hydroxide layers of Sample No. 1. In other words, $CO_3^{2-}$ may have been incorporated in the structure of the nickel hydroxide layers.

Sample No. 3 ($PO_4^{3-}$) showed the smallest weight loss. It is considered that $PO_4^{3-}$ did not readily split within the temperature range at which TGA was performed and $PO_4^{3-}$ was incorporated in the structure of the nickel hydroxide layers.

Sample No. 4 ($B_4O_7^{2-}$) was not expected to undergo thermal decomposition. For this reason, TGA-FTIR was not performed for Sample No. 4 ($B_4O_7^{2-}$).

The TGA profile of Sample No. 5 (oxalate ions) is similar to the TGA profile of Sample No. 1 ($SO_4^{2-}$). The FTIR data suggests that the first-step and the second-step weight losses were accompanied by release of $H_2O$ and $CO_2$. Further, the FTIR data suggests that the third-step weight loss was accompanied by release of $SO_2$. Therefore, it is considered that oxalate ions were not incorporated in the structure of the nickel hydroxide layers.

In Table 1 below, "negative" under "TGA-FTIR incorporation" indicates that the polyatomic anions may have not been incorporated in the structure of the nickel hydroxide layers. In Sample No. 5, $SO_4^{2-}$ instead of oxalate ions may have been incorporated in the nickel hydroxide layers.

Sample No. 6 (citrate ions) before hydrothermal treatment showed the greatest weight loss among all the samples. 40% of the weight loss occurred at 100 to 400° C. The temperature range of 100 to 400° C. agrees with the reported decomposition temperature of nickel citrate. Further, the FTIR data suggests that the weight loss at 100 to 400° C. was accompanied by release of carbon monoxide (CO), $H_2O$, and $CO_2$. It is considered that the CO came from an organic substance. These results suggest that citrate ions were incorporated in the structure of the nickel hydroxide layers.

The weight loss of Sample No. 6 after hydrothermal treatment is smaller than the weight loss of Sample No. 6 before hydrothermal treatment. It is considered that the hydrothermal treatment caused dissociation of citrate ions from the nickel hydroxide layers.

<<Operating Potential (Potential at 0.4 Capacity)>>

Positive electrodes including the nickel hydroxide of Samples Nos. 1 to 6 were prepared. These positive electrodes were for alkaline battery use. The operating potential (discharge potential) was measured, with a mercury oxide electrode (Hg/HgO) used as a reference electrode. Results are shown in Table 1 below. The values of potential listed under "Potential at 0.4 capacity" in Table 1 below were measured when the remaining capacity of the positive electrode was 0.4 relative to the full-discharged capacity of the positive electrode defined as 1.

<<Memory Effect (Memory V Drop)>>

The positive electrode was stored at 50° C. for 48 hours while being charged to maintain the potential of the positive electrode at 0.35 to 0.37 V (vs Hg/HgO). After storage, the positive electrode was discharged for voltage drop (V drop) measurement. Results are shown in Table 1 below. The smaller the voltage drop is, the less likely the memory effect may have been to occur.

For all the samples, hydrothermal treatment tended to decrease FWHM; in other words, hydrothermal treatment tended to increase crystallinity. As the crystallinity increased, the operating potential tended to increase.

As for Sample No. 5 (oxalate ions), oxalate ions may have not been incorporated in the nickel hydroxide layers. As for Sample No. 5, this may have caused an increase in crystallinity and thereby an increase in operating potential.

The crystallinity of the sample in which polyatomic anions may have been incorporated in the nickel hydroxide layers (No. 1 to 4, 6) is lower than the crystallinity of Sample No. 5. It is considered that $OH^-$ in the nickel hydroxide layers was partially replaced by the polyatomic anions to cause a structural defect, leading to the decrease in crystallinity. Therefore, the above-mentioned change in operating potential may have been caused by incorporation of the polyatomic anions, independent of the level of crystallinity.

The crystallinity of Sample No. 4 ($B_4O_7^{2-}$) (for which TGA-FTIR was not performed) was low, like the other samples with incorporation (Samples Nos. 1 to 3, 6). Therefore, with Sample No. 4 ($B_4O_7^{2-}$), $B_4O_7^{2-}$ may have been incorporated in the nickel hydroxide layers.

Experiment 2

In Experiment 2, incorporation of polyatomic anions in the nickel hydroxide layers was studied. In Experiment 2, the second raw material liquid (raw material liquid not containing $SO_4^{2-}$) was studied.

<<(A) Preparing Raw Material Liquid and (B) Synthesizing>>

(Sample No. 8)

A reaction vessel was prepared. In the reaction vessel, 1 M aqueous solution of $Ni(NO_3)_2$ (20 mL) was added. While the aqueous solution of $Ni(NO_3)_2$ was being swiftly stirred with a magnetic stirrer at room temperature, 2 M aqueous

TABLE 1

Synthesis for the case of using precursor salt not free of $SO_4^{2-}$

| | First raw material liquid (Precursor) | | | | Before hydrothermal treatment | | | | | After hydrothermal treatment | | | |
|---|---|---|---|---|---|---|---|---|---|---|---|---|---|
| | 0.2M aq | | | | | XRD | | Potential | | | XRD | Potential | |
| No. | 1M aq NiSO$_4$/ mL | Na-Anion salt/ mL | 2M aq NaOH/ mL | Anion | phase | FWHM [011]/ ° | TGA-FTIR incorporation | at 0.4 capacity/ V | Memory V drop/ mV | phase | FWHM [011]/ ° | at 0.4 capacity/ V | Memory V drop/ mV |
| 1 | 20 | 20 | 25 | SO$_4^{2-}$ | β | n/a*² | positive | 0.323 | 13 | β | 2.6 | 0.339 | 16 |
| 2 | 20 | 20 | 22 | CO$_3^{2-}$ | β | n/a | positive | 0.324 | 13 | β | 2.3 | 0.338 | 14 |
| 3 | 20 | 20 | 20 | PO$_4^{3-}$ | β | n/a | positive | 0.319 | 11 | β | 1.9 | 0.326 | 16 |
| 4 | 20 | 20*¹ | 22 | B$_4$O$_7^{2-}$ | β | n/a | — | 0.321 | 16 | β | 2.9 | 0.334 | 16 |
| 5 | 20 | 20 | 23 | Oxalate ions | β | 4.1 | negative | 0.332 | 16 | β | 1.1 | 0.345 | 19 |
| 6 | 20 | 20 | 20 | Citrate ions | β | n/a | positive | 0.331 | 12 | β | 2.7 | 0.333 | 13 |

*¹0.02M aq
*²not applicable

<<Results of Experiment 1>>

As illustrated in Table 1 above, the operating potential of the sample with the particular polyatomic anions incorporated in the nickel hydroxide layers (Samples Nos. 3, 4, and 6) is different from the operating potential of the sample with $SO_4^{2-}$ and $CO_3^{2-}$ incorporated in the nickel hydroxide layers (Samples Nos. 1 and 2). With inorganic anions (Samples Nos. 3 and 4), the operating potential decreased. With organic anions (Sample No. 6), the operating potential increased. With Sample No. 6 (citrate ions), the memory effect tended not to occur.

solution of NaOH (20 mL) was added into the reaction vessel. Thus, the second raw material liquid was prepared. The final pH of the second raw material liquid was adjusted to 11.5. By this pH adjustment, the nickel hydroxide of Sample No. 8 was synthesized. The nickel hydroxide was collected. After collected, the nickel hydroxide was rinsed with water and dried in air.

(Samples Nos. 7 and 9)

As specified in Table 2 below, instead of the aqueous solution of $Ni(NO_3)_2$, each of an aqueous solution of $NiSO_4$ and an aqueous solution of nickel acetate was used to synthesize the nickel hydroxide of Samples Nos. 7 and 9. The amount of each aqueous solution added was as specified in Table 2 below.

Sample No. 7 is a control. Although containing $SO_4^{2-}$, the raw material liquid of Sample No. 7 is regarded as the second raw material liquid for the sake of convenience.

<<XRD>>

For Samples Nos. 7 to 9, XRD patterns of the nickel hydroxide were checked. The XRD patterns of Samples Nos. 7 and 9 show β-Ni(OH)$_2$ structure. In the XRD pattern of Sample No. 8, α-Ni(OH)$_2$ structure and β-Ni(OH)$_2$ structure coexist. The FWHM of [001] peak was used to evaluate crystallinity. Results are shown in Table 2 below. The smaller the FWHM is, the higher the crystallinity may be.

Figure 5:
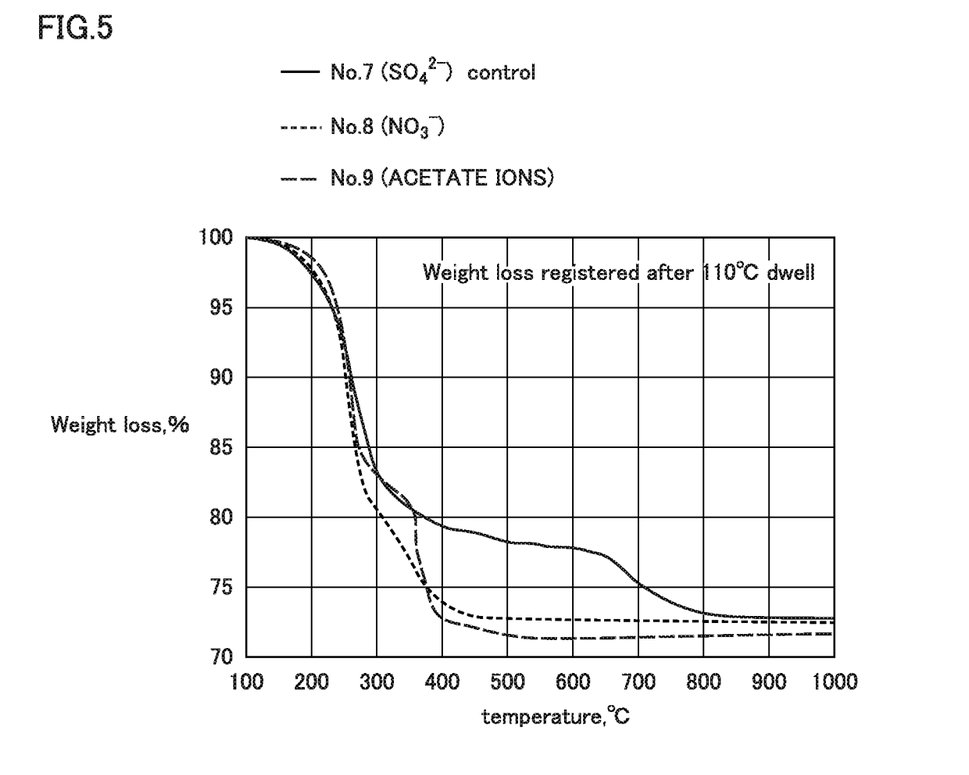
FIG. 5 illustrates TGA profiles of Samples Nos. 7 to 9.

FIG. 5 illustrates TGA profiles of Samples Nos. 7 to 9.

Also in this experiment, the samples were subjected to pretreatment at 110° C. for 80 minutes.

The TGA profile of Sample No. 7 ($SO_4^{2-}$) is substantially the same as the TGA profile of Sample No. 1 ($SO_4^{2-}$).

Sample No. 8 ($NO_3^-$) showed a weight loss in two steps. The first-step weight loss occurred at 270 to 360° C. The second-step weight loss occurred at 360 to 400° C. The second-step weight loss is very small. The FTIR data indicates no gas generation attributed to $NO_3^-$. The FTIR data suggests that the weight loss at 400° C. or lower was accompanied by release of $H_2O$ and $CO_2$. These results suggest that $NO_3^-$ was not incorporated in the structure of the nickel hydroxide layers.

Sample No. 9 (acetate ions) showed a weight loss in two steps. The first-step weight loss occurred at 270 to 360° C. The second-step weight loss occurred at 360 to 400° C. The FTIR data suggests that the first-step weight loss was accompanied by release of $H_2O$ and $CO_2$ and the second-step weight loss was accompanied by release of a small amount of $H_2O$ and a great amount of $CO_2$. The second-step weight loss may have been caused by splitting of acetate ions. These results suggest that acetate ions were incorporated in the structure of the nickel hydroxide layers.

<<Operating Potential (Potential at 0.4 Capacity)>>

In the same manner as in Experiment 1, positive electrodes including the nickel hydroxide of Samples Nos. 7 to 9 were prepared and the operating potential was measured. Results are shown in Table 2 below.

<<Memory Effect (Memory V Drop)>>

In the same manner as in Experiment 1, voltage drop (V drop) was measured. Results are shown in Table 2 below.

<<Results of Experiment 2>>

As illustrated in Table 2 above, the operating potential of the sample with the particular polyatomic anions incorporated in the nickel hydroxide layers (Sample No. 9) is different from the operating potential of the sample with $SO_4^{2-}$ incorporated in the nickel hydroxide layers (Sample No. 7).

The XRD patterns and FWHM suggest that Sample No. 9 (acetate ions) has the highest crystallinity among the samples without hydrothermal treatment. One of the reasons may be that the acetate salt had a low acidity and therefore the pH tended to be maintained within the target range during synthesis.

Experiment 3

In Experiment 3, the relationship between the amount of replacement by citrate ions and the memory effect was investigated.

<<(A) Preparing Raw Material Liquid and (B) Synthesizing>>

(Sample No. 11)

A reaction vessel was prepared. In the reaction vessel, 1 M aqueous solution of $NH_4OH$ (250 mL) was added. In the reaction vessel, 1 M aqueous solution of $NiSO_4$ (10 mL) was further added. The reaction vessel was left at 55° C. for 4 hours or longer.

Then, 0.05 M aqueous solution of sodium citrate, 2.4 M aqueous solution of NaOH, 0.0236 M aqueous solution of $Na_2CO_3$, and 1 M aqueous solution of $NH_4OH$ were added into the reaction vessel. These aqueous solutions were added simultaneously at a rate of 10 mL/h. Thus, the first raw material liquid was prepared. The final pH of the first raw material liquid was adjusted to 12 to 13. Thus, the nickel hydroxide of Sample No. 11 was synthesized. The nickel hydroxide was collected. After collected, the nickel hydroxide was rinsed with water and dried in air.

(Samples Nos. 10, 12, and 13)

The concentration of the aqueous solution of sodium citrate was changed to achieve the feed composition specified in Table 3 below, and thus the nickel hydroxides of Nos. 10, 12, and 13 were synthesized. Sample No. 10 is a control.

<<Memory Test>>

In the same manner as in Experiment 1, positive electrodes including the nickel hydroxide of Samples Nos. 10 to 13 were prepared, and the initial operating potential was measured. Subsequently, each positive electrode was stored at 50° C. while being charged to maintain the potential of the positive electrode at 0.35 to 0.37 V (vs Hg/HgO). At 48 hours and 120 hours of storage, the operating potential

TABLE 2

Synthesis for the case of using $SO_4^{2-}$-free precursor salt

| | Second raw material liquid (Precursor) | | | | Before hydrothermal treatment | | | |
|---|---|---|---|---|---|---|---|---|
| | Aqueous solution of | | | | XRD | | | |
| | salt | | 2M aq | | | | | |
| No. | Ni-Anion salt | 1M aq/ mL | NaOH/ mL | Anion | phase | FWHM [001]/ ° | TGA-FTIR incorporation | Potential at 0.4 capacity/V | Memory Voltage drop/ mV |
| 7 | $NiSO_4$ | 20 | 25 | $SO_4^{2-}$ | β | n/a | positive | 0.323 | 13 |
| 8 | $Ni(NO_3)_2$ | 20 | 20 | $NO_3^-$ | α/β | n/a | negative | 0.318 | 15 |
| 9 | $Ni(CH_3COO)_2$ | 20 | 17 | Acetate ions | β | 4 | positive | 0.330 | 12 |

(Potential) and the voltage drop (V drop) were measured. Results are shown in Table 3 below.

TABLE 3

Memory test results of citrate samples

| Formula No. (feed composition) | Anion | Memory test condition | Potential at 0.4 capacity/V | Memory V drop/ mV |
|---|---|---|---|---|
| 10 $Ni(OH)_{1.60}(Anion)_{0.20}$ | $SO_4^{2-}$ | 50° C., 48 h | 0.322 | 12 |
|  |  | 50° C., 120 h | 0.330 | 18 |
| 11 $Ni(OH)_{1.85}(Anion)_{0.05}$ | Citrate ions | 50° C., 48 h | 0.321 | 6 |
|  |  | 50° C., 120 h | 0.327 | 13 |
| 12 $Ni(OH)_{1.70}(Anion)_{0.10}$ | Citrate ions | 50° C., 48 h | 0.320 | 6 |
|  |  | 50° C., 120 h | 0.325 | 8 |
| 13 $Ni(OH)_{1.40}(Anion)_{0.20}$ | Citrate ions | 50° C., 48 h | 0.331 | 12 |
|  |  | 50° C., 120 h | 0.334 | 12 |

<<Results of Experiment 3>>

As illustrated in Table 3 above, when citrate ions were incorporated in the nickel hydroxide layers, the memory effect tended not to occur. Particularly when the amount of replacement in the nickel hydroxide is from 5 mol % to 10 mol % (Samples Nos. 11 and 12), the memory effect tended not to occur. It is considered that this tendency is noticeable at 120 hours of storage.

Experiment 4

Studied in Experiment 4 is a nickel hydroxide in which $OH^-$ in the nickel hydroxide layers was partially replaced by polyatomic anions and $Ni^{2+}$ was partially replaced by $Al^{3+}$.

<<(A) Preparing Raw Material Liquid and (B) Synthesizing>>

(Sample No. 17)

A reaction vessel was prepared. In the reaction vessel, 2 M aqueous solution of NaOH (20 mL) was added. While the aqueous solution of NaOH was being swiftly stirred with a magnetic stirrer, 0.125 M aqueous solution of $Al_2(SO_4)_3$ (20 mL), 0.75 M aqueous solution of $NiSO_4$ (20 mL), and 0.2 M aqueous solution of sodium citrate (20 mL) were added into the reaction vessel. Thus, the first raw material liquid was prepared. In order to adjust the pH of the first raw material liquid to the range of 11 to 12, 2 M aqueous solution of NaOH was added thereto as appropriate. Thus, the nickel hydroxide of Sample No. 17 was synthesized.

(Samples Nos. 14 to 16)

Instead of the aqueous solution of sodium citrate, each of an aqueous solution of $Na_2SO_4$, an aqueous solution of sodium oxalate, and an aqueous solution of sodium acetate was used so that the polyatomic anions specified in Table 4 below were incorporated in the nickel hydroxide layers, and thus the nickel hydroxide of Nos. 14 to 16 was synthesized.

<<(C) Hydrothermal Treatment>>

As for the nickel hydroxide of Nos. 14 and 17, samples with hydrothermal treatment were also synthesized. The treatment temperature was 100° C. The treatment time was 24 hours.

<<TGA-IR>>

TGA-IR was performed to check if polyatomic anions were incorporated. Results are shown in Table 4 below.

<<Operating Potential (Potential at 0.4 Capacity)>>

In the same manner as in Experiment 1, the operating potential was measured. Results are shown in Table 4 below.

TABLE 4

Properties of anion and cation ($Al^{3+}$) incorporated samples

| No. Formula (feed composition) | Anion | Before hydrothermal treatment | | After hydrothermal treatment |
|---|---|---|---|---|
|  |  | TGA-FTIR incorporation | Potential at 0.4 capacity/V | Potential at 0.4 capacity/V |
| 14 $Ni_{0.75}Al_{0.25}(OH)_{1.60}(Anion)_{0.20}$ | $SO_4^{2-}$ | positive | 0.320 | 0.362 |
| 15 $Ni_{0.75}Al_{0.25}(OH)_{1.80}(Anion)_{0.20}$ | Acetate ions | positive | 0.325 | — |
| 16 $Ni_{0.75}Al_{0.25}(OH)_{1.60}(Anion)_{0.20}$ | Oxalate ions | negative | 0.337 | — |
| 17 $Ni_{0.75}Al_{0.25}(OH)_{1.40}(Anion)_{0.20}$ | Citrate ions | positive | 0.328 | 0.344 |

<<Results of Experiment 4>>

As illustrated in Table 4 above, for the sample with partial replacement of $Ni^{2+}$ by $Al^{3+}$, incorporation of polyatomic anions tended to change the operating potential.

The hydrothermal treatment tended to cause an increase in operating potential. Comparison of Samples Nos. 1 and 6 (Table 1) with Samples Nos. 14 and 17 (Table 4) indicates that the sample with partial replacement of $Ni^{2+}$ by $Al^{3+}$ shows a marked increase in operating potential after hydrothermal treatment.

The embodiments and examples disclosed herein are illustrative and non-restrictive in any respect. The technical scope indicated by the claims encompasses any modifications within the scope and meaning equivalent to the terms of the claims.

What is claimed is:

1. A nickel hydroxide comprising stacked nickel hydroxide layers,
    each of the nickel hydroxide layers including nickel ions and hydroxide ions,
    at least one of the nickel hydroxide layers further including a type of polyatomic anions,
    the polyatomic anions including a type of anions that are not sulfate ions or carbonate ions and a type of organic anions,
    wherein the organic anions include citrate ions.

2. The nickel hydroxide according to claim 1, wherein the polyatomic anions include a type of inorganic anions.

3. The nickel hydroxide according to claim 2, wherein the inorganic anions include at least one type selected from the group consisting of phosphate ions and tetraborate ions.

4. The nickel hydroxide according to claim 1, wherein at least one of the nickel hydroxide layers further includes aluminum ions.

5. A positive electrode material comprising at least the nickel hydroxide according to claim 1.

6. An alkaline battery comprising at least the positive electrode material according to claim 5.

7. A method of producing a nickel hydroxide according to claim 1, comprising:
    (A) preparing a raw material liquid containing at least nickel ions, hydroxide ions, and a type of polyatomic anions comprising citrate ions; and
    (B) synthesizing a nickel hydroxide by adjusting a pH of the raw material liquid, the method further comprising
    (C) performing hydrothermal treatment on the nickel hydroxide.

8. The method of producing a nickel hydroxide according to claim 7, wherein the raw material liquid is prepared by mixing an aqueous solution of nickel sulfate, an aqueous solution of a salt of sodium ions and the polyatomic anions, and an aqueous solution of sodium hydroxide.

9. The method of producing a nickel hydroxide according to claim 7, wherein the raw material liquid is prepared by mixing an aqueous solution of a salt of nickel ions and the polyatomic anions and an aqueous solution of sodium hydroxide.

10. The method of producing a nickel hydroxide according to claim 7, wherein the polyatomic anions include a type of inorganic anions.

11. The method of producing a nickel hydroxide according to claim 10, wherein the inorganic anions include at least one type selected from the group consisting of phosphate ions and tetraborate ions.

12. The method of producing a nickel hydroxide according to claim 7, wherein the raw material liquid further contains aluminum ions.

* * * * *